April 27, 1976
N. BULL
KALANCHOE PLANT
Filed Dec. 20, 1974
Plant Pat. 3,873
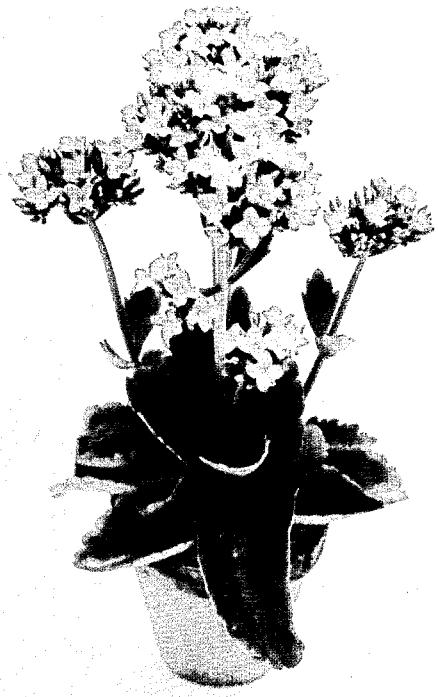

United States Patent

Plant Pat. 3,873
Patented Apr. 27, 1976

3,873

KALANCHOE PLANT

Norbert Bull, Gonnebek, Germany, assignor to Mikkelsens, Inc., Ashtabula, Ohio

Filed Dec. 20, 1974, Ser. No. 535,200

Int. Cl. Plt.—68 1 Claim

The present invention relates to a new and distinct variety of Kalanchoe plant known by the varietal name Granat.

The new variety was discovered by me as a selected, cultivated seedling resulting from a cross between B101, the unnamed seed parent, and B103, the unnamed pollen parent. The new cultivar was asexually reproduced by stem cuttings at Gonnebek, West Germany, and the unique characteristics of the new cultivar have been transmitted through successive propagations.

The new cultivar is particularly characterized by its bright deep red flowers which possess strong luminous power and in which the white pistil is prominently contrasted. The new cultivar is further characterized by its large unbels, very strong stem, its relatively large blooms which reach a size of 20 mm., and by its long keeping qualities.

The natural blooming season of the new cultivar is late January to early February, although by steered culturing in the greenhouse, the cultivar can be brought to flowering during the entire year. Flowering response, as controlled by the initiation of short day treatment, is 12 weeks in summer and 16–18 weeks in winter. The time from sticking of cuttings to flowering is 20 or 28 weeks for summer and winter, respectively.

The accompanying color photographic drawing shows a typical blooming plant of the new cultivar, with the color being as true as possible with color illustrations of this type.

The following is a detailed description of my new Kalanchoe variety based on plants produced under commercial practices grown in 12 cm. pots maturing in mid July. Color references are made to the Royal Horticultural Society Colour Chart except where general terms of ordinary dictionary significance are used.

PARENTAGE

The new cultivar is a seedling resulting from crossing the seed parent B101, an unnamed and unpatented variety, with the pollen parent B103, also an unnamed and unpatented Kalanchoe variety.

PROPAGATION

Asexually propagates true to type.

(A) *Type cutting*: 15 mm. to 25 mm. long terminal cutting.

(B) *Time to root*: 10–12 days at 24° C., summer.

(B) *Time to root*:
10–12 days at 24° C., summer.
15–18 days at 20° C., winter.

(C) *Rooting habit*: Typical for commercial cultivars having a profusion of fibrous dendritic roots. This cultivar is the most massive rooting of my four Kalanchoe cultivars for which patent applications have been filed, with the other cultivars being disclosed in pending application Ser. Nos. 535,199 (Cherie); 535,128 (Korall) and 535,087 (Roter Pfeffer), all of which were filed Dec. 20, 1974.

PLANT DESCRIPTION (A) *Form*: Very compact, erect, close internodes, heavy large dense foliage. Secondary shoots and/or flower peduncles are vigorous and stiff, measuring upwards of 5 mm. to 8 mm. in diameter. Although plant is compact, when flowering the added upright vigor of the peduncles gives the plant an overall tall appearance.

(B) *Habit of growth*: Medium to strong vigorous growing habit with limited self branching. Removal of apical tip forces a limited number of side shoots averaging 6.

(C) *Foliage description*: Generally would be considered very large, heavily textured, dark green color, good placement to be distinctive.

(1) *Size*: 10–12 cm. wide to 12–14 cm. long with considerable longitudinal cupping to appear elliptical, petiole 25 to 30 mm. long.

(2) *Shape*: Quite oval to elliptical from immature to mature stages—distinct in that leaf shape is maintained continuously.

(3) *Texture*: Thick, fleshy, coriaceous, underside, glabrous.

(4) *Margin*: Heavily crenated to double crenated.

(5) *Color*: Young foliage, top side, yellow green 147B; underside, yellow green 147C; mature foliage: top side, yellow green between 146A and 147B, underside, near 147C.

FLOWERING DESCRIPTION (A) *Flowering habits*: Flowering is irregular over two to three or more months time. The large individual flowers offset the lower number of flowers in bloom at any one time. Inflorescence has irregular shape as compared to ball type form of Korall or flat rounded form of Cherie.

(B) *Natural flowering season*: In nothern latitudes, mid to late January. Flowering time under controlled daylength at 22° C. in summer is 12–13 weeks; in winter is 14 weeks.

(C) *Flower bud description*: Flower buds are approximately 3 mm. in diameter by 6–7 mm. long before opening. On opening the flower is 15–18 mm. deep, 4 green sepals.

(D) *Flowers borne*: On compound paniculate cymes. The primary peduncles are 25–30 cm. long and 5 to 8 mm. in diameter. Secondary peduncles occur in opposite pairs and vary in length from 3 to 6 cm. in length. Individual flower pedicels are 5 mm. long.

(E) *Quality of flowers*: Compared to Korall, Granat appeared to be considerably less in number because of opening irregularly over long period of time. Actual bud count indicates 14 or more in each secondary game.

(F) *Petals*: Nearly elliptical measuring 7 mm. wide x 10–11 mm. long.

(1) *Shape*: Total flowers diameter 20 mm. or more.

(2) *Color*: Top side, when opening, 44AB in summer, fading to red 43 AB, underside, red 52C.

(3) *Number of petals*: Four, nearly flat, very little overlapping.

(G) *Reproductive organs*:

(1) *Stamens*: Number generally eight, occasionally nine or ten.

(a) *Anther shape*: Typical, color, medium to dark brown.

(b) *Filament*: Color, light yellow green.
(c) *Pollen*: Color, yellow.

(2) *Pistils*:
(a) *Stigma shape*: Round, flat often coalesced to 2–3 mm. in diameter; color, white to pink when receptive.
(b) *Style color*: Yellowish translucent.
(c) *Ovaries*: Four in number; size 2–3 mm. in diameter; color, green; many ovaries have secondary styles without stigmas.

DISEASE RESISTANCE

Apparently immune to mildew when grown with susceptible varieties infected with this disease; more susceptible to botrytis infection than Korall, Roter Pfeffer, or Cherie.

I claim:

1. A new and distinct variety of Kalanchoe plant characterized particularly by its bright deep red flowers which possess strong luminous power and in which a bulging white pistil is prominently contrasted; large umbels on very strong stems; relatively large blooms, and by its long keeping qualities.

No references cited.

ROBERT E. BAGWILL, Primary Examiner

UNITED STATES PATENT AND TRADEMARK OFFICE

CERTIFICATE OF CORRECTION

PATENT NO. : PP-3,873
DATED : April 27, 1976
INVENTOR(S) : NORBERT BULL

It is certified that error appears in the above-identified patent and that said Letters Patent are hereby corrected as shown below:

Column 2, line 53, "game" should be --cyme--.

Signed and Sealed this

Seventeenth Day of August 1976

[SEAL]

*Attest:*

RUTH C. MASON
*Attesting Officer*

C. MARSHALL DANN
*Commissioner of Patents and Trademarks*